US012599322B2

(12) United States Patent
Zou et al.

(10) Patent No.: US 12,599,322 B2
(45) Date of Patent: Apr. 14, 2026

(54) METHOD FOR AN ANALYTE SENSOR COVER-MEMBRANE PREPARATION

(71) Applicant: Roche Diabetes Care, Inc., Indianapolis, IN (US)

(72) Inventors: Peng Zou, Ludwigshafen am Rhein (DE); Alexander Steck, Hirschberg (DE); Gernot Hochmuth, Mannheim (DE); Reinhold Mischler, Ludwigshafen (DE); Kirill Sliozberg, Mannheim (DE); Christian Hoertz, Worms (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 1196 days.

(21) Appl. No.: 17/519,858

(22) Filed: Nov. 5, 2021

(65) Prior Publication Data

US 2022/0054059 A1 Feb. 24, 2022

Related U.S. Application Data

(63) Continuation of application No. PCT/EP2020/062270, filed on May 4, 2020.

(30) Foreign Application Priority Data

May 6, 2019 (EP) .................................... 19172715

(51) Int. Cl.
*C08J 3/24* (2006.01)
*A61B 5/1486* (2006.01)

(52) U.S. Cl.
CPC .... *A61B 5/14865* (2013.01); *A61B 2562/125* (2013.01)

(58) Field of Classification Search
CPC .......................................................... C08J 3/24
See application file for complete search history.

(56) References Cited

U.S. PATENT DOCUMENTS

| | | | | |
|---|---|---|---|---|
| 8,277,713 | B2 * | 10/2012 | Petisce | A61B 5/14865 264/650 |
| 8,632,877 | B2 | 1/2014 | Opperman | |
| 2001/0056301 | A1 * | 12/2001 | Goupil | A61B 17/1219 424/78.18 |
| 2005/0242479 | A1 * | 11/2005 | Petisce | A61B 5/14865 264/650 |
| 2006/0292701 | A1 * | 12/2006 | Huang | C08J 7/043 436/514 |
| 2008/0277276 | A1 * | 11/2008 | Gardner | C12Q 1/002 204/403.06 |
| 2013/0052456 | A1 * | 2/2013 | Opperman | B01D 67/0088 428/220 |
| 2015/0001074 | A1 | 1/2015 | Liu | |
| 2015/0025168 | A1 * | 1/2015 | Lienkamp | A61L 2/232 521/149 |
| 2017/0115280 | A1 | 4/2017 | Hazen et al. | |

FOREIGN PATENT DOCUMENTS

| | | | | |
|---|---|---|---|---|
| WO | WO 2007/147475 A1 | | 12/2007 | |
| WO | WO-2008018879 A1 | * | 2/2008 | B01D 71/701 |
| WO | WO 2010/028708 A1 | | 3/2010 | |
| WO | WO 2012/019083 A2 | | 2/2012 | |

OTHER PUBLICATIONS

International Search Report and Written Opinion of the International Searching Authority, PCT/EP2020/062270, Sep. 22, 2020, 19 pages.

* cited by examiner

*Primary Examiner* — Cachet I Proctor
(74) *Attorney, Agent, or Firm* — Bose McKinney & Evans LLP

(57) ABSTRACT

This disclosure relates to a process for forming a membrane on an analyte sensor and further relates to an analyte sensor obtainable by this process. This disclosure also relates to a process for forming a sensing layer on an electrode of an analyte sensor and to an analyte sensor having the sensing layer obtainable by the inventive process as well as the membrane obtainable by the inventive process. The analyte sensors obtainable by the inventive processes may be used for conducting an analyte measurement of a body fluid of a user or a patient. This disclosure may be applied in the field of home care as well as in the field of professional care, such as in hospitals. Other applications are generally feasible.

5 Claims, No Drawings

METHOD FOR AN ANALYTE SENSOR COVER-MEMBRANE PREPARATION

RELATED APPLICATIONS

This application is a continuation of PCT/EP2020/062270, filed May 4, 2020, which claims priority to EP 19 172 715.5, filed May 6, 2019, the entire disclosures of both of which are hereby incorporated herein by reference.

BACKGROUND

This disclosure relates to a process for forming a membrane on an analyte sensor. This disclosure further relates to an analyte sensor obtainable by this process. Furthermore, this disclosure relates to a process for forming a sensing layer on an electrode of an analyte sensor and to an analyte sensor comprising the sensing layer obtainable by the inventive process as well as the membrane obtainable by the inventive process. The analyte sensors obtainable by the inventive processes may mainly be used for conducting at least one analyte measurement of a bodily fluid of a user or a patient. This disclosure may both be applied in the field of home care as well as in the field of professional care, such as in hospitals. Other applications are generally feasible.

Biosensors for measuring analyte in biological fluids, in particular, a sensor which is designed for implantation to measure body fluids, have to fulfill a variety of functions. On the one hand, the sensor must provide for specific and sensitive measurement without interference from, e.g., particular components of body fluids, such as cells. For this purpose, biosensors are frequently covered with membranes excluding particular compounds in order to allow access to the actual sensing sites only for low molecular weight compounds. Moreover, with implanted sensors, it is preferred to have sensors which can remain in place for a long period without deterioration of the measurement, in order to spare the patient from frequently exchanging the sensor.

Implanted sensors, for example, comprise electrode systems which facilitate measurements of physiologically significant analytes such as, for example, glucose in the patient's body. The working electrodes of such a sensor have electrically conductive enzyme layers in which enzyme molecules are bound which release charge carriers by catalytic conversion of the analyte molecules. In this process, an electrical current is generated as a measuring signal whose amplitude correlates to the analyte concentration. These types of sensors are also called electrochemical sensors.

Such electrochemical sensors are known from, e.g., WO 2007/147475 and WO 2010/028708. The working electrodes of these electrode systems are provided with a diffusion barrier that controls the diffusion of the analyte to be determined from the body fluid or tissue surrounding the electrochemical sensor to the enzyme molecules that are immobilized in the enzyme layer. WO 2007/147475 discloses a diffusion barrier made from a polymer having a zwitterionic structure.

WO 2012/019083 discloses a diffusion limiting membrane comprising a polyurethane, a siloxane and a hydrogel. The membrane is prepared by first mixing the polymers, then depositing the polymers onto the sensor and subsequently evaporating the solvent.

The sensors disclosed in the prior art have only limited long-term stability, especially in in vivo applications.

SUMMARY AND DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

This disclosure teaches improved means and methods for forming membranes on an analyte sensor and avoids at least in part the drawbacks of the prior art, in particular, with regard to long-term stability and membrane performance.

Advantages are obtained by the process for forming a membrane on an analyte sensor as well as the analyte sensor obtainable by this process and by the process for forming a sensing layer on an electrode of an analyte sensor and by an analyte sensor comprising the sensing layer obtainable by the inventive process and the membrane obtainable by the inventive process. Preferred embodiments which may be realized in an isolated way or in an arbitrary combination are disclosed in the dependent claims and throughout the application.

As used in the following, the terms "have," "comprise," or "include" or any arbitrary grammatical variations thereof are used in an exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it should be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "polymer," "cross-linkable group," and "solvent," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restrictions regarding alternative embodiments of the invention, without any restrictions regarding the scope of the invention and without any restrictions regarding the possibility of combining the features introduced in such way with the optional or nonfunctional features of the invention.

In a first aspect of this disclosure, a process for forming a membrane on an analyte sensor is disclosed, the process comprising the following steps:

a) providing the analyte sensor,
b) providing a polymer solution which comprises:
   (A) at least one first polymer which comprises at least one first cross-linkable group,
   (B) at least one second polymer which comprises at least one second cross-linkable group and
   (C) at least one first solvent,
c) contacting the analyte sensor provided in step a) with the polymer solution, provided in step b) to obtain an analyte sensor which is coated with the polymer solution,
d) drying the analyte sensor obtained in step c) to obtain the dried analyte sensor which is coated with a polymer blend which comprises the at least one first polymer and the at least one second polymer,
e) curing the polymer blend which coats the dried analyte sensor obtained in step d) whereby the at least one first polymer and the at least one second polymer are cross-linked to form the membrane on the analyte sensor.

Herein, the indicated steps may, preferably, be performed in the given order, thereby commencing with process step a) and finishing with process step e), wherein, however any or all of the indicated steps, in particular process steps a) and b), may be performed at least partially concurrently and/or step b) may be performed before step a). Further, additional process steps, whether described herein are not, may be performed, too.

As further used herein, the term "analyte" may refer to an arbitrary element, component or compound which may be present in a body fluid and the concentration of which may be of interest for a user. Preferably, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be used and/or any combination of analytes may be determined. Preferably, the analyte is glucose.

As generally used, the term "analyte sensor" may refer to any device being configured for the detection of an analyte. Preferably, the analyte sensor is a biosensor. Further preferably, the analyte sensor is an electrochemical sensor. The term "electrochemical sensor" refers to a sensor which is adapted for performing at least one electrochemical measurement, in particular, a plurality or series of electrochemical measurements, in order to detect the at least one analyte comprised within the body fluid by using an amperometric method. Especially, the term "electrochemical measurement" refers to a detection of an electrochemically detectable property of the analyte, such as an electrochemical detection reaction, by employing amperometric methods. Thus, for example, the electrochemical detection reaction may be carried out by applying and comparing one or more electrode potentials. Thus, the analyte sensor preferably comprises an electrode. Specifically, the electrochemical sensor may be adapted to generate at least one electrical measurement signal which may directly or indirectly indicate the presence and/or absence of the electrochemical detection reaction, such as at least one current signal and/or at least one voltage signal. The measurement may be a qualitative and/or a quantitative measurement. Still, other embodiments are feasible.

In particular, the analyte sensor comprises an electrode. The electrode may be embodied in the manner that oxidative processes and/or reductive processes may take place at selected surfaces of the electrode. This electrode is in one embodiment a working electrode. In a particularly preferred embodiment as used herein, the analyte sensor has a working electrode, a reference electrode, and a counter electrode, wherein both the working electrode and the reference electrode may be covered by a membrane, wherein the working electrode further includes an enzyme, wherein the working electrode may comprise the enzyme or may be covered by an enzyme layer.

If the analyte sensor is an electrochemical sensor it preferably comprises an electrode system. In an embodiment the analyte sensor comprises a working electrode with immobilized enzyme molecules for the conversion of the analyte which results in the generation of an electrical signal. The enzymes may be present in a layer covering the electrode. This layer is in one embodiment a sensing layer. A process for the forming of the sensing layer will be described in more detail below. Additionally, redox mediators and/or electrochemical catalysts as well as carbon particles and porous particles may be present in or on the working electrode. This type of electrode is described, e.g., in WO 2007/147475, the entire disclosure of which is hereby incorporated herein by reference.

In a particularly preferred embodiment, the analyte sensor may be fully or partially implantable and may, thus, be adapted for performing the detection of the analyte in the body fluid in a subcutaneous tissue, in particular, in an interstitial fluid. As used herein the terms "implantable" or "subcutaneous" refer to being fully or at least partially arranged within the body tissue of the patient or the user. For this purpose, the analyte sensor may comprise an insertable portion, wherein the term "insertable portion" may generally refer to a part or component of an element configured to be insertable into an arbitrary body tissue while other parts or components may remain outside of the body tissue. Preferably, the insertable portion may fully or partially comprise a biocompatible surface, i.e., a surface which may have as little detrimental effects on the user, the patient, or the body tissue as possible, at least during typical durations of use. In an embodiment, the biocompatible surface is the membrane obtainable by the inventive process.

As generally used, the term "body fluid" may refer to fluid, in particular liquid, which may typically be present in a body or a body tissue of the user or the patient and/or which may be produced by the body of the user or the patient. Preferably, the body fluid may be blood or interstitial fluid. However, additionally or alternatively, one or more other types of body fluid may be used, such as saliva, tear fluid, urine or other body fluids. During the detection of the at least one analyte, the body fluid may be present within the body or body tissue. Thus, the analyte sensor may at least be configured for detecting the at least one analyte within the body tissue. The analyte sensor is in one embodiment suitable for short-term application, e.g., 3 to 21 days, or for long-term application, e.g., 1 to 12 months. During its application, the analyte may be determined by continuous or discontinuous measurements.

In step a) of the process for forming a membrane on an analyte sensor of this disclosure, the analyte sensor is provided.

The analyte sensor in an embodiment comprises at least one substrate and comprises at least one first electrode. The at least one first electrode is in an embodiment at least one working electrode and is adapted for detecting the analyte. The analyte sensor generally may be dimensioned such that a transcutaneous insertion is feasible, such as by providing a width in a direction perpendicular to an insertion direction of no more than 5 mm, preferably of no more than 2 mm, more preferably of no more than 1.5 mm. The sensor may have a length of less than 50 mm, such as a length of 30 mm or less, e.g., a length of 5 mm to 30 mm. It shall be noted, however, that other dimensions are feasible.

The analyte sensor may comprise a sensing layer obtainable by the inventive process for forming a sensing layer on a first electrode of an analyte sensor as described below.

In step b) the polymer solution is provided. The polymer solution comprises components (A), at least one first polymer which comprises at least one first cross-linkable group, (B), at least one second polymer which comprises at least one second cross-linkable group, and (C), at least one first solvent.

components (A), (B) and (C), preferably based on the total weight of the polymer solution.

To the person skilled in the art, it is clear that the mol-% relates to the amount of components (A) and (B) before they have reacted with one another. It is furthermore clear that, for example, during the drying in step d) and/or curing in step e) the molar ratio between the components may change.

The polymer solution can additionally comprise a component (Ba), at least one further polymer comprising at least one third cross-linkable group. For the at least one third cross-linkable group, the embodiments and preferences described below for the at least one first cross-linkable group hold true.

The optional component (Ba) is different from components (A) and (B). A suitable at least one further polymer is for example polyethylene glycol with benzophenone as the at least one cross-linkable group. Polyethylene glycol with benzophenone as the at least one cross-linkable group is also called PEG-BP. One suitable PEG-BP is shown in figure (I):

(I)

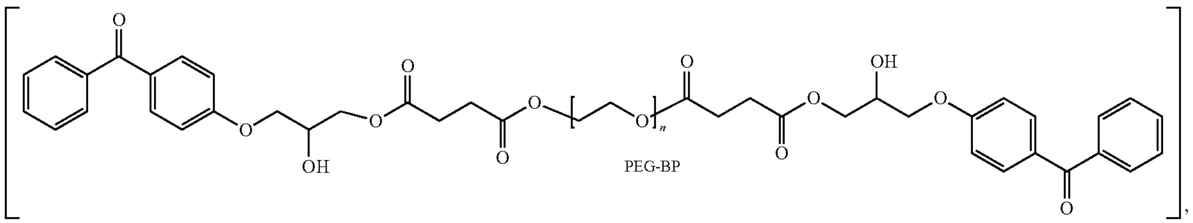

PEG-BP

Within the context of this disclosure, the terms "component (A)" and "at least one first polymer which comprises at least one first cross-linkable group" are used synonymously and, therefore, have the same meaning.

Furthermore, within the context of this disclosure, the terms "component (B)" and "at least one second polymer which comprises at least one second cross-linkable group" are used synonymously and, therefore, have the same meaning.

Within the context of this disclosure, the terms "component (C)" and "at least one solvent" are used synonymously and, therefore, have the same meaning.

In step b), the polymer solution can be provided by any method known. For example, component (A) and component (B) can be added to component (C) optionally while stirring component (C). In an embodiment, component (C) is heated to a solving temperature (Ts) while components (A) and (B) are added to component (C). For example, the solving temperature (Ts) is in the range from 0 to 50° C.

In an embodiment, the polymer solution comprises in the range from 30 to 99.5 mol-% of component (A), preferably in the range from 50 to 99 mol-%, based on the sum of the mol-% of components (A) and (B).

In an embodiment, the polymer solution is in the range from 0.5 to 70 mol-% of component (B), preferably in the range from 1 to 50 mol-%, based on the sum of the mol-% of components (A) and (B).

The sum of the mol-% of components (A) and (B) usually add up to 100 mol-%.

In an embodiment, the polymer solution is in the range of from 1 to 50 wt.-% of component (C), preferably in the range from 5 to 30 wt.-%, based on the total weight of wherein n is in the range from 100 to 10000, preferably in the range from 200 to 5000.

In an embodiment, the polymer solution comprises at least one cross-linker. The at least one cross-linker is different from components (A), (B) and optional (Ba). The at least one cross-linker is an oligomeric or monomeric, preferably a monomeric compound. Suitable cross linkers are for example selected from the group consisting of epoxides, thiol comprising cross-linkers, benzophenone comprising cross-linkers, anhydrides and imides.

A suitable epoxide is, for example, glycidyl glycerol ether.

Suitable thiol-comprising cross-linkers are for example selected from the group consisting of 1,2-ethane dithiol, 1,3-propane trithiol, ethane-1,1,2,2-tetrathiol, ethene-1,1,2,2-tetrathiol, pentaerythryltetrathiol (=2,2-bis(mercaptomethyl)propane-1,3-dithiol), 2,2'-(ethylenedioxy)diethanethiol, tetra(ethylene glycol)dithiol, hexa(ethylene glycol) dithiol, 1,4-benzenedimethanethiol, 2,2-bis(sulfanylmethyl)propane-1,3-dithiol, benzene-1,2,4,5-tetrathiol and SH-functionalized nanopartides.

In an embodiment of this disclosure, the polymer solution provided in step ii) does not comprise at least one cross-linker. In an embodiment, the polymer solution provided in step ii) consists of components (A), (B) and (C) and optionally component (Ba).

Within the context of this disclosure, the term "polymer solution" means not only a solution in its ordinary and customary meaning but also heterogeneous mixtures, such as a colloidal solution or a suspension. "A solution" means that components (A), (B) and (C) form a homogeneous mixture (i.e., one phase). A solution does not allow beams of light to scatter and the solute (components (A) and (B)) cannot be separated from the solvent (component (C)) by filtration. "Colloidal solution" and "suspension" mean that components (A) and (B) are in their solid state and are suspended in component (C). Thus, components (A) and (B) form a dispersed phase (suspended particles) and component (C) forms a continuous phase (medium of suspension). The particles of the dispersed phase in a colloidal solution have a diameter between approximately 1 and 1000 nm. The particles of the dispersed phase in a suspension have a diameter of greater than 1000 nm. Preferably the term "polymer solution" relates to a solution in which components (A), (B) and (C) form a homogeneous mixture.

Component (A) is at least one first polymer which comprises at least one first cross-linkable group. For example, the at least one first polymer is in the range from 0.5 to 20 mol-% of the at least one first cross-linkable group, preferably in the range from 2 to 8 mol-% of the at least one first cross-linkable group based on the sum of the mol-% of the at least one first polymer and the at least one first cross-linkable group, preferably based on the total amount of component (A).

The at least one first cross-linkable group is directly linked to the at least one first polymer. The at least one first cross-linkable group is in an embodiment a group which forms radicals when it is heated and/or exposed to light.

For example, the at least one first cross-linkable group is selected from the group consisting of benzophenone groups, azide groups, anthrachinone groups, and psoralen.

Suitable azide groups are, for example selected from the group consisting of sulfonyl azide groups, phenyl azide, ortho-hydroxyphenyl azide, meta-hydroxyphenyl azide, tetraflurophenyl azide, ortho-nitrophenyl azide, meta-nitrophenyl azide, diazirine, and azido-methylcoumarine.

The at least one first polymer is a homopolymer or a copolymer. Suitable copolymers are block copolymers or statistical copolymers. A block copolymer comprises at least two different blocks, wherein each block is prepared from at least one type of monomers, whereas a statistical copolymer comprises a sequence of units prepared from different monomers following a statistical rule. If the copolymer is prepared from monomer X and monomer Y, then a block copolymer comprises a block prepared only from monomer X and a block prepared only from monomer Y. In a statistical copolymer, for example three units prepared from monomer X are followed by five units prepared from monomer Y which are followed by two units prepared from monomer X which are followed by one unit prepared from monomer Y and so on.

For example, the at least one first polymer is a hydrophobic polymer.

For example, the at least one first polymer is selected from the group consisting of ethyl acrylate (EA), n-propyl acrylate, i-propyl acrylate, n-butyl acrylate (n-BuA), sec-butyl acrylate (sec-BuA), i-butyl acrylate (i-BuA), 3-pentyl acrylate, n-pentyl acrylate, n-hexyl acrylate, n-hexyl methacrylate, 2-ethylhexyl acrylate, 2-ethylhexyl methacrylate, n-heptyl acrylate, n-heptyl methacrylate, n-octyl acrylate, n-octyl methacrylate, n-nonyl acrylate, n-nonyl methacrylate, n-decyl methacrylate, iso-decyl methacrylate, n-dodecyl methacrylate, n-dodecyl acrylate, polyurethanes, styrene and combinations thereof.

Component (B) is at least one second polymer which comprises at least one second cross-linkable group. For example, the at least one second polymer is in the range from 0.5 to 20 mol-%, preferably in the range from 2 to 8 mol-% of the at least one second cross-linkable group based on the sum of the mol-% of the at least one second polymer and the at least one second cross-linkable group, preferably based on the total amount of component (B).

For the at least one second cross-linkable group the embodiments and preferences described above for the at least one first cross-linkable group hold true.

Thus, the at least one second cross-linkable group is in an embodiment a group which forms radicals when it is heated and/or exposed to light. The at least one second cross-linkable group is directly linked to the at least one second polymer.

The at least one second cross-linkable group is for example selected from the group consisting of benzophenone groups, azide groups, anthrachinone groups, and psoralen.

For the azide groups the above-described embodiments hold true.

Therefore, in an embodiment of the inventive process the at least one first cross-linkable group and the at least one second cross-linkable group are independently of one another selected from the group consisting of benzophenone groups, azide groups, anthrachinone groups, and psoralen.

The at least one second polymer is different from the at least one first polymer. Within the context of this disclosure, "different" means that the at least one first polymer and the at least one second polymer differ for example in their properties and/or in the type of the at least one first polymer and the at least one second polymer.

The at least one second polymer is a homopolymer or a copolymer. Suitable copolymers are block copolymers or statistical copolymers. For the block copolymer and the statistical copolymer, the embodiments and preferences described above for the at least one first polymer hold true.

In an embodiment, the at least one second polymer is a hydrophilic polymer.

For example, the at least one second polymer is selected from the group consisting of polyvinylpyrrolidone (PVP), side-chain functionalized polyvinylpyrrolidone, 2-hydroxyethyl acrylate, 2-hydroxyethyl methacrylate (HEMA), 2-methoxyethyl acrylate, 2-methoxyethyl methacrylate, 2-ethoxyethyl acrylate, 2-ethoxyethyl methacrylate, 2-hydroxypropyl acrylate, 3-hydroxypropyl acrylate, 2-hydroxypropyl methacrylate (2-HPMA), 3-hydroxypropyl methacrylate (3-HPMA), 2-methoxypropyl acrylate, 3-methoxypropyl acrylate, 2-methoxypropyl methacrylate, 3-methoxypropyl methacrylate, 2-ethoxypropyl acrylate, 3-ethoxypropyl acrylate, 2-ethoxypropyl methacrylate, 3-ethoxypropyl methacrylate, 1-glycerol acrylate, 2-glycerol acrylate, 1-glycerol methacrylate, 2-glycerol methacrylate, acrylamide, methacrylamide, N-alkyl acrylamide, N,N-dialkyl acrylamide, N-alkyl methacrylamide and N,N-dialkyl methacrylamide, wherein alkyl comprises methyl, ethyl or propyl, acrylic acid, methacrylic acid and combinations thereof.

In an embodiment, the at least one second polymer fulfils at least one of the following requirements:

- the at least one second polymer further fine tunes the hydrophobicity of the membrane,
- the at least one second polymer reduces the diffusion of unwanted substances through the membrane,
- the at least one second polymer improves bioactivities of the membrane, such as antifouling and/or biocompatibility.

Component (C) is at least one first solvent. Suitable first solvents are solvents in which components (A) and (B) can be dissolved or suspended. Therefore the at least one first solvent is preferably selected from polar solvents.

Suitable polar solvents are selected from the group consisting of polar protic solvents and polar aprotic solvents.

Suitable polar protic solvents are for example selected from the group consisting of water, methanol, ethanol and isopropyl alcohol.

Suitable polar aprotic solvents are for example selected from the group consisting of dichlormethane, tetrahydrofurane (THF), ethylacetate and dimethyl carbonate (DMC).

Therefore, in one embodiment the at least one first solvent is selected from the group consisting of water, methanol, ethanol, tetrahydrofurane (THF), and dimethyl carbonate (DMC).

Therefore, in an embodiment of the process of this disclosure for forming a membrane on an analyte sensor, component (C), the at least one first solvent, is selected from the group consisting of water, methanol, ethanol, tetrahydrofurane (THF), and dimethyl carbonate (DMC).

In step c) the analyte sensor provided in step a) is contacted with the polymer solution provided in step b) to obtain an analyte sensor which is coated with the polymer solution.

The analyte sensor can be contacted with the polymer solution by any method. For example, the analyte sensor can be contacted with the polymer solution by dipping or immersing the analyte sensor into the polymer solution. It is also possible to contact the analyte sensor with the polymer solution by spray coating or doctor blading the analyte sensor with the polymer solution. Thus, in an embodiment, the contacting of the analyte sensor with the polymer solution in step c) is carried out by dipping, spray coating, immersing and/or doctor blading.

In step c) the analyte sensor which is coated with the polymer solution is obtained. This means, by contacting the analyte sensor with the polymer solution an analyte sensor coated with the polymer solution is obtained.

The analyte sensor is at least partially coated with the polymer solution. As described above, in an embodiment, the analyte sensor is an electrochemical sensor. In this case, preferably at least the working electrode is coated with the polymer solution. In an embodiment, the analyte sensor is an electrochemical sensor and only the working electrode is coated with the polymer solution. In an embodiment, the analyte sensor is fully coated with the polymer solution. In an embodiment, the analyte sensor is an electrochemical sensor and is fully coated with the polymer solution. "Fully coated" within the context of this disclosure means that at least the part of the sensor, which is within the body of the subject during the use of the sensor, is coated with the polymer solution.

The thickness of the coating of the polymer solution on the analyte sensor is for example in the range from 1 to 100 μm.

In step d) the analyte sensor obtained in step c) is dried to obtain a dried analyte sensor which is coated with a polymer blend. The polymer blend comprises the at least one first polymer and the at least one second polymer.

If the polymer solution provided in step b) additionally comprised component (Ba), at least one further polymer comprising at least one third cross-linkable group, then the polymer blend which coats the dried analyte sensor, additionally comprises the component (Ba).

The analyte sensor can be dried under reduced pressure, for example in vacuum.

Alternatively or additionally, the drying of the analyte sensor in step d) can be carried out by heating. For example, the analyte sensor obtained in step c) can be heated to a drying temperature ($T_D$). The drying temperature ($T_D$) is usually lower than the curing temperature ($T_C$) at which the polymer blend cures.

This means that the drying temperature ($T_D$) is below the temperature for forming radicals from the at least one first cross-linkable group and/or the at least one second cross-linkable group. For example, the drying temperature ($T_D$) in step d) is in the range from 15 to 80° C.

During the drying in step d) the at least one solvent (component (C)) is evaporated. This means that the at least one solvent is removed from the polymer solution. Thereby the polymer blend is obtained.

Preferably, during the drying, the polymer blend is not cured. This means that during the drying step preferably the at least one first polymer and the at least one second polymer, as well as the at least one first cross-linkable group and the at least one second cross-linkable group do not react with one another.

In step e), the polymer blend which coats the dried analyte sensor obtained in step d) is cured. Thereby the at least one first polymer and the at least one second polymer are cross-linked to form the membrane on the analyte sensor.

During the curing in step e) the at least one first cross-linkable group comprised in the at least one first polymer and the at least one second cross-linkable group comprised in the at least one second polymer are reacted. The at least one first cross-linkable group and the at least one second cross-linkable group can each be cross-linked with itself as well as with one another. This means that the at least one first cross-linkable group can be cross-linked with another first cross-linkable group as well as with the at least one second cross-linkable group. On the other hand, the at least one second cross-linkable group can be cross-linked with the at least one first cross-linkable group as well as with another second cross-linkable group.

During the curing step, the at least one first polymer and the at least one second polymer are linked to one another. Additionally, the at least one first polymer is cross-linked with itself and with the second polymer. The same holds true for the at least one second polymer. The at least one second polymer is cross-linked with itself and also with the at least one first polymer. In an embodiment it is possible that the at least one first polymer and/or the at least one second polymer are also linked to the analyte sensor. In an embodiment, the at least one first polymer and/or the at least one second polymer are linked to the analyte sensor via the at least one first cross-linkable group and/or the at least one second cross-linkable group.

The curing in step e) can be carried out for example by heating the dried analyte sensor obtained in step d) or by exposing the analyte sensor obtained in step d) to light. This means that the polymer blend which covers the dried analyte sensor is heated or exposed to light.

In an embodiment of the inventive process therefore the curing in step e) comprises at least one of heating the polymer blend and exposing the polymer blend to light.

If the curing in step e) is carried out by heating the polymer blend then the dried analyte sensor obtained in step d) (i.e., the polymer blend covering the dried analyte sensor) is heated to a curing temperature ($T_C$). The curing temperature ($T_C$) is typically above the drying temperature ($T_D$) in step d). In an embodiment, at the curing temperature ($T_C$), the at least one first cross-linkable group and/or the at least one second cross-linkable group usually form radicals. In particular, if one of the at least one first cross-linkable group and the at least one second cross-linkable group comprises N (nitrogen) and the other one of the at least one first cross-linkable group and the at least one second cross-linkable group comprises an epoxide group, then at the curing temperature ($T_C$) the at least one first cross linkable group reacts with the at least one second cross-linkable group. The formation of radicals is then not mandatory.

The curing temperature ($T_C$) is usually in the range from 20 to 100° C.

If the curing in step e) is carried out by exposing the dried analyte sensor obtained in step d) (i.e., the polymer blend covering the dried analyte sensor) to light, any wavelength of the light can be used which does not cleave the bonds within the at least one first polymer and/or the at least one second polymer. Preferably the wavelength is in the range of UV light. This means that the wavelength of the light is preferably in the range of from 200 to 400 nm.

In step e) the membrane on the analyte sensor is obtained. In an embodiment, the membrane coats the analyte sensor at least partially. Usually the membrane coats the analyte sensor in the same region as the polymer solution in step c). In an embodiment, in particular if the curing is carried out by exposing the analyte sensor (i.e., the polymer blend covering the dried analyte sensor) to light, only selected regions of the analyte sensor are cured. In particular, preferably the regions in the region of the working electrodes are cured if the analyte sensor is an electrochemical sensor. In this case, the curing is preferably carried out by light. It is possible that the uncured regions of the analyte sensor (i.e., the regions which were not exposed to light) are removed after step e).

The membrane has for example a thickness in the range from 1 to 100 μm.

The membrane in an embodiment of this disclosure is a diffusion limiting membrane. The diffusion limiting membrane is also called a diffusion barrier. A diffusion limiting membrane controls the diffusion of the analyte from body fluid surrounding the analyte sensor to the enzyme molecules which are in one embodiment of this disclosure comprised in the sensing layer of the analyte sensor.

Another object of this disclosure is an analyte sensor obtainable by the inventive process.

The inventive process is particularly advantageous as it allows an easy manufacturing of a membrane on an analyte sensor. Preferably, the analyte sensor is coated with the membrane. Additionally, the properties of the membrane can be easily tailored based on the at least one first polymer and the at least one second polymer. The obtained membrane is well defined and has a long-term stable structure. In particular, if the membrane is also covalently immobilized on the sensor surface the durability of the analyte sensor for in vivo applications is particularly improved. Also, the properties of the obtained membrane are easier to predict.

In a second aspect of this disclosure, a process for forming a sensing layer on a first electrode of an analyte sensor is disclosed, the method comprises the steps:

i) providing an analyte sensor comprising at least one first electrode, wherein the first electrode comprises a first electrode material,
ii) reacting the at least one first electrode of the analyte sensor provided in step i) with a functionalizing compound which comprises at least one first group which is reactive towards the first electrode material and at least one second group which is cross-linkable, to obtain at least one functionalized first electrode,
iii) providing a polymer mixture comprising
   (D) at least one mediator polymer which comprises at least one cross-linkable group,
   (E) is at least one second solvent,
iv) contacting the at least one functionalized first electrode obtained in step ii) with the polymer mixture provided in step iii) to obtain at least one coated functionalized first electrode,
v) drying the at least one coated functionalized first electrode obtained in step iv) to obtain at least one dried coated first electrode which is coated with the at least one mediator polymer,
vi) curing the at least one dried coated first electrode, whereby the at least one second group of the functionalizing compound and the at least one cross-linkable group of the at least one mediator polymer are cross-linked to form the sensing layer on the electrode of the analyte sensor.

Herein, the indicated steps i) to vi) may, preferably, be performed in the given order, thereby commencing with process step i) and finishing with process step vi), wherein, however any or all of the indicated steps, in particular process steps i) and iii), may be performed at least partially concurrently and/or step iii) may be performed before step i). Further, additional process steps, whether described herein or not, may be performed, too.

In step i) an analyte sensor is provided. For the analyte sensor the embodiments and preferences described above for the analyte sensor provided in step a) of the inventive process for forming a membrane on an analyte sensor hold true. The analyte sensor comprises at least one first electrode. In an embodiment, the at least one first electrode is at least one working electrode. The at least one first electrode comprises a first electrode material. The first electrode material comprises in one embodiment a conductive material. For example, the first electrode material is selected from the group consisting of metals, metal oxides and carbon.

Preferably, the first electrode material is a metal. Suitable metals are for example selected from the group consisting of gold, copper, palladium, iridium, silver, and an alloy thereof. Suitable metal oxides are for example selected from the group consisting of iridium-tin oxides.

In an embodiment of the process for forming a sensing layer on an electrode of an analyte sensor, the first electrode material comprises at least one metal. In a further embodiment of the process for forming a sensing layer on an electrode of an analyte sensor the first electrode material comprises gold.

In a preferred embodiment, the analyte sensor is an electrochemical sensor which is arranged in the fashion of an electrochemical cell. Thus, it employs at least one pair of electrodes. As generally used, the term "electrode" refers to an entity of the analyte sensor which is adapted to contact the body fluid.

In step ii) the at least one first electrode of the analyte sensor provided in step i) is reacted with a functionalizing compound to obtain at least one functionalized first electrode. The functionalizing compound comprises at least one first group which is reactive towards the first electrode material and at least one second group which is cross-linkable.

The first group which is reactive towards the first electrode material is selected so that it can react with the first electrode material. In an embodiment, the at least one first group is selected from the group consisting of silane groups, thiol groups and disulfide groups.

The at least one second group which is cross-linkable is in an embodiment a group which forms radicals when it is heated and/or exposed to light. For the at least one second group the embodiments and preferences described above for the at least one first cross-linkable group and the at least one second cross-linkable group hold true. Thus, for example, the at least one second group which is cross-linkable is selected from the group consisting of benzophenone groups, azide groups, anthrachinone groups, and psoralen.

For the azide groups the above-described embodiments hold true.

Within the functionalizing compound the at least one first group is preferably linked to the at least one second group via a spacer. Suitable spacers are for example selected from the group consisting of substituted or unsubstituted $C_2$-$C_{12}$-alkandiyls.

Therefore, in an embodiment of this disclosure, the functionalizing compound is selected from the group consisting of triethoxysilane benzophenone, (4-benzoylbenzoyl)aminopropyltrimethoxy silane, (4-benzoylbenzoyl)aminoethyltrimethoxy silane, 4-(3'-chlorodimethylsilyl)propyloxybenzophenone, and 4-hydroxybenzophenone 1,2-Dithiolane-3-pentanoate (Lipoic Acid Benzophenone Ester).

The reacting of the at least one first electrode with the functionalizing compound in step ii) can be carried out by any method. For example, first the at least one first electrode can be coated with the functionalizing compound optionally in the presence of at least one solvent. Second, the reaction between the first electrode material and the first group of the functionalizing compound can be initiated. The at least one solvent is, for example an apolar solvent, such as toluene.

The temperature during the reacting in step ii) is for example in the range from 0 to 40° C.

During the reaction of the at least one first electrode of the analyte sensor with the functionalizing compound, the first electrode material of the at least one first electrode reacts with the at least one first group which is reactive towards the first electrode material thereby forming a covalent bond between the functionalizing compound and the first electrode material. The obtained functionalized first electrode comprises the at least one second group which is cross-linkable of the functionalizing compound on its surface. This means that the at least one second group which is cross-linkable can further react. Preferably, the at least one second group which is cross-linkable does not react with the first electrode material.

In step iii) a polymer mixture is provided. The polymer mixture comprises components (D), at least one mediator polymer which comprises at least one cross-linkable group, and (E) the at least one second solvent.

Within the context of this disclosure the term "polymer mixture" relates to a solution in its ordinary and customary meaning and also to a colloidal solution or suspension of component (D) with component (E). The term "solution" means that components (D) and (E) form a homogeneous mixture (i.e., one phase). A solution does not allow beams of light to scatter and the solute (component (D)) cannot be separated from the solvent (component (E)) by filtration. The terms "colloidal solution" and "suspension" mean that component (D) is in its solid state and that it is suspended in component (E). Thus, component (D) forms the dispersed phase (suspended particles) and component (E) forms the continuous phase (medium of suspension). The dispersed phase particles in a colloidal solution have a diameter between approximately 1 and 1000 nm. The dispersed phase particles in a suspension have a diameter of greater than 1000 nm. Preferably, the polymer mixture is a solution, in which components (D) and (E) form a homogeneous mixture.

For example, the polymer mixture comprises in the range from 2 to 10 weight-% of component (D), based on the total weight of components (D) and (E), preferably based on the total weight of the polymer mixture.

For example, the polymer mixture comprises in the range from 90 to 98 weight-% of component (E), based on the total weight of components (D) and (E), preferably based on the total weight of the polymer mixture.

In an embodiment the polymer mixture provided in step iii) additionally comprises at least one enzyme. For example, the polymer mixture then comprises in the range from 2 to 10 weight-% of the at least one enzyme based on the total weight of the polymer mixture.

The weight-% of components (D) and (E) usually add up to 100 weight-%. If the polymer mixture additionally comprises at least one enzyme, then the weight-% of components (D) and (E) as well as of the at least one enzyme add up to 100 weight-%.

Typically, the at least one enzyme is an oxidoreductase, i.e., an enzyme catalyzing a redox reaction. Particularly, the enzyme catalyzes a redox reaction wherein $H_2O_2$ is generated and/or consumed. More particularly, the enzyme catalyzes a reaction wherein $H_2O_2$ is generated, e.g., from $O_2$ as a co-substrate. Specific examples of such enzymes are glucose oxidase (EC 1.1.3.4), hexose oxidase (EC 1.1.3.5), cholesterol oxidase (EC 1.1.3.6), galactose oxidase (EC 1.1.3.9), alcohol oxidase (EC 1.1.3.13), (S)-2 hydroxy acid oxidase (EC 1.1.3.15), L-glutamate oxidase (EC 1.4.3.11)), or L-aspartate oxidase (EC 1.4.3.16). Particularly, the enzyme is glucose oxidase, e.g., glucose oxidase from *Aspergillus* or *Penicillium*.

Component (E) is at least one second solvent. Suitable second solvents are solvents in which component (D) can be dissolved or suspended. Therefore, the at least one second solvent is preferably selected from protic polar solvents.

Suitable protic polar solvents are selected from the group consisting of water, methanol, and ethanol.

Component (D) is at least one mediator polymer which comprises at least one cross-linkable group. For the at least one cross-linkable group comprised in the at least one mediator polymer, the embodiments and preferences described above for the at least one second group which is cross-linkable and which is comprised in the functionalizing compound holds true. Therefore the at least one cross-linkable group is preferably selected from the group consisting of benzophenone groups, azide groups, anthrachinone groups, and psoralen.

For the azide groups the above-described embodiments hold true.

"At least one mediator polymer" within the context of this disclosure means a polymer which comprises a mediator compound. In an embodiment, the mediator compound is a redox mediator.

Within the context of this disclosure, a "redox mediator" is understood to transfer electrons from the enzyme active center to the surface of the at least one first electrode.

In an embodiment, the at least one mediator polymer comprises a mediator compound selected from the group consisting of a ruthenium-containing complex and an osmium-containing complex. Thus, in one embodiment, this disclosure relates to a process for forming a sensing layer on an electrode of an analyte sensor in which component (D), the at least one mediator polymer, comprises a redox mediator selected from the group consisting of a ruthenium-containing complex and an osmium-containing complex.

Preferably, the at least one mediator polymer is a statistical copolymer of at least two different types of polymers.

The polymer mixture provided in step iii) can additionally comprise a component (Da), at least one second further polymer comprising at least one second further cross-linkable group. For the at least one second further cross-linkable group the embodiments and preferences described above for the at least one cross-linkable group comprised in the at least one mediator polymer hold true.

The at least one second further polymer is different from the at least one mediator polymer.

Preferably, the polymer mixture does not additionally comprise a component (Da), at least one second further polymer.

In step iv) the at least one functionalized first electrode obtained in step ii) is contacted with the polymer mixture provided in step iii). Thereby at least one coated functionalized first electrode is obtained.

The at least one functionalized first electrode can be contacted with the polymer mixture by any known method. For example, the at least one functionalized first electrode can be contacted with the polymer mixture by dipping or immersing the at least one functionalized first electrode into the polymer mixture. It is also possible to contact the functionalized first electrode with the polymer mixture by spray coating or doctor blading the functionalized first electrode. It is also possible to contact the analyte sensor with the polymer mixture and thereby also contacting the at least one functionalized first electrode with the polymer mixture.

In step iv) at least one coated functionalized first electrode is obtained. This means by contacting the functionalized first electrode with the polymer mixture the coated functionalized first electrode is obtained.

The thickness of the polymer mixture coating the at least one functionalized first electrode is for example in the range from 0.1 to 5 μm.

In step v) the at least one coated functionalized first electrode is dried to obtain a dried coated first electrode which is coated with at least one mediator polymer.

The coated functionalized first electrode can be dried under reduced pressure for example in vacuum.

Alternatively or additionally, the drying of the coated functionalized first electrode in step v) can be carried out by heating. For example, the coated functionalized first electrode obtained in step iv) can be heated to a drying temperature ($T_{D2}$). The drying temperature ($T_{D2}$) is usually lower than the temperature at which the dried coated first electrode cures. This means that the drying temperature ($T_{D2}$) is below the curing temperature ($T_{C2}$). For example, the drying temperature ($T_{D2}$) in step v) is in the range from 0 to 40° C.

During the drying in step v) the at least one second solvent (component (E)) evaporates. This means that the at least one second solvent is removed from the polymer mixture. Thereby the coating of the at least one mediator polymer is obtained.

The coating of the at least one mediator polymer can additionally comprise residues of component (E), the at least one second solvent. For example, the coating of the at least one mediator polymer may comprise in the range from <1 wt-% of the at least one second solvent based on the total weight of the coating of the at least one mediator polymer.

Preferably during the drying step v) the mediator polymer and/or the at least one dried coated first electrode are not cured. This means that during the drying step preferably the at least one dried coated first electrode and the at least one mediator polymer do not react with one another.

In step vi) the at least one dried coated first electrode is cured. Thereby the at least one second group of the functionalizing compound and the at least one cross-linkable group of the at least one mediator polymer are cross-linked to form the sensing layer on the electrode of the analyte sensor.

During the curing in step vi) the at least one second group of the functionalizing compound and the at least one cross-linkable group of the at least one mediator polymer are reacted with one another. The at least one second group of the functionalizing compound and the at least one cross-linkable group of the at least one mediator polymer can each be cross-linked with itself as well as with one another.

During the curing step, the at least one mediator polymer is linked to the surface of the at least one first electrode.

If in one embodiment of this disclosure the polymer mixture provided in step iii) comprises component (Da) at least one second further polymer, then also the at least one second further polymer is reacted with the at least one mediator polymer and the at least one second group of the functionalizing compound. In this embodiment typically the at least one second further polymer and the at least one mediator polymer are cross-linked.

If the polymer mixture comprised at least one enzyme then the obtained sensing layer usually comprises the at least one enzyme as well. In an embodiment, the at least one enzyme is dispersed within the layer of the mediator polymer and optionally the at least one second further polymer.

The curing in step vi) can be carried out for example by heating the at least one dried coated first electrode obtained in step v) or by exposing the at least one dried coated first electrode obtained in step v) to light. This means that the mediator polymer which coats the at least one dried coated first electrode is heated or exposed to light.

In an embodiment of the inventive process therefore the curing in step vi) comprises at least one of heating the at least one dried coated first electrode and exposing the at least one dried coated first electrode to light.

If the curing in step vi) is carried out by heating the at least one dried coated first electrode then the at least one dried coated first electrode obtained in step v) is heated to a curing temperature ($T_{C2}$). The curing temperature ($T_{C2}$) is typically above the drying temperature ($T_{D2}$) in step v). At the curing temperature ($T_{C2}$) the at least one second group of the functionalizing compound and/or the at least one cross-linkable group usually form radicals.

The curing temperature ($T_{C2}$) is usually in the range from 20 to 100° C.

If the curing in step vi) is carried out by exposing the at least one dried coated first electrode obtained in step v) to light, then any wavelength of the light can be used which does not cleave the bonds within the functionalizing compound and/or the at least one mediator polymer. Preferably, the wavelength of the light is in the range of UV light. This means that the wavelength of the light is preferably in the range of from 200 to 400 nm.

In an embodiment of this disclosure, in a first step the sensing layer is formed on an electrode of the analyte sensor according to the inventive process for forming a sensing layer on an electrode of an analyte sensor. In a second step the membrane is formed on the analyte sensor comprising the sensing layer on the electrode according to inventive the process for forming a membrane on an analyte sensor.

Thus, this disclosure also discloses an analyte sensor comprising a sensing layer obtainable by the process for forming a sensing layer on a first electrode of an analyte sensor according to this disclosure and a membrane obtainable by the process for forming a membrane on analyte sensor.

In an embodiment the membrane at least partially covers the sensing layer of this analyte sensor.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A process for forming a membrane on an analyte sensor, comprising:

a) providing the analyte sensor;

b) providing a polymer solution which comprises (i) a first polymer that is hydrophobic and has a first cross-linkable group, (ii) a second polymer that is hydrophilic and has a second cross-linkable group, and (iii) a first solvent;

c) contacting the analyte sensor provided in step a) with the polymer solution provided in step b) to obtain an analyte sensor which is coated with the polymer solution;

d) drying the analyte sensor obtained in step c) to obtain a dried analyte sensor which is coated with a polymer blend which comprises the first polymer and the second polymer; and e) curing the polymer blend which coats the dried analyte sensor obtained in step d), whereby the first polymer and the second polymer are cross-linked to form the membrane on the analyte sensor, wherein the first cross-linkable group and the second cross-linkable group are independently of one another selected from the group consisting of benzophenone groups, azide groups, anthrachinone groups, and psoralen; and f) wherein the second polymer is different from the first polymer.

2. The process according to claim 1, wherein the curing in step e) comprises at least one of heating the polymer blend and exposing the polymer blend to light.

3. The process according to claim 1, wherein the first solvent is selected from the group consisting of water, methanol, ethanol, tetrahydrofurane, and dimethyl carbonate.

4. The process according to claim 1, wherein the first polymer is a homopolymer.

5. The process according to claim 1, wherein the second polymer is a homopolymer.

* * * * *